United States Patent
Creighton

(10) Patent No.: US 6,940,379 B2
(45) Date of Patent: Sep. 6, 2005

(54) MAGNETS WITH VARYING MAGNETIZATION DIRECTION AND METHOD OF MAKING SUCH MAGNETS

(75) Inventor: Francis M. Creighton, Clayton, MO (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 10/082,715

(22) Filed: Feb. 25, 2002

(65) Prior Publication Data

US 2002/0113678 A1 Aug. 22, 2002

Related U.S. Application Data

(63) Continuation of application No. 09/546,840, filed on Apr. 11, 2000, now abandoned.

(51) Int. Cl.[7] ................................................. H01F 7/02
(52) U.S. Cl. ............................ 335/306; 335/298; 600/1; 600/424
(58) Field of Search ......................... 335/216, 296–299, 335/302–306; 600/1, 407, 424, 429

(56) References Cited

U.S. PATENT DOCUMENTS

| | | | |
|---|---|---|---|
| 5,216,400 A | * | 6/1993 | Leupold ..................... 335/306 |
| 5,257,636 A | | 11/1993 | White |
| 5,312,321 A | | 5/1994 | Holcomb |
| 5,523,732 A | * | 6/1996 | Leupold ..................... 335/306 |
| 5,622,169 A | | 4/1997 | Golden et al. |
| 5,681,260 A | | 10/1997 | Ueda et al. |
| 5,711,299 A | * | 1/1998 | Manwaring et al. ........ 600/417 |

* cited by examiner

Primary Examiner—Lincoln Donovan
(74) Attorney, Agent, or Firm—Harness Dickey & Pierce PLC

(57) ABSTRACT

A permanent magnet in which the magnetization direction varies with location to optimize or restrict a magnetic field property in a selected direction at a selected point. The magnetic field property may be, for example, the transverse magnetic field, axial magnetic field, axial gradient of the transverse magnetic field, transverse gradient of the transverse magnetic field, axis gradient of the axial magnetic field, transverse gradient of the axial magnetic field, the product of the transverse magnetic field and the transverse gradient of the transverse magnetic field, the product of the transverse magnetic field and the axial gradient of the transverse magnetic field, the product of the axial magnetic field and the transverse gradient of the axial magnetic field, or the product of the axial magnetic field and the axial gradient of the axial magnetic field. The magnet may be formed of one or more segments in which the magnetization direction varies smoothly and continuously, or the magnet may be formed of a plurality of segments in which the magnetization direction is constant. A method of making and using such magnets is also disclosed.

17 Claims, 9 Drawing Sheets

US 6,940,379 B2

MAGNETS WITH VARYING MAGNETIZATION DIRECTION AND METHOD OF MAKING SUCH MAGNETS

This application is a continuation of application Ser. No. 09/546,840, field Apr. 11, 2000, now abandoned.

FIELD OF THE INVENTION

This invention relates to permanent magnets, and in particular to a permanent magnet in which the magnetization direction varies to maximize a selected magnetic property of the magnet, and to methods of making such magnets.

BACKGROUND OF THE INVENTION

There are a number of applications, such as magnetic surgical applications, where it necessary to apply strong magnetic forces (i.e., magnetic fields and/or gradients). With recent advances in permanent materials, permanent magnets can provide strong magnetic forces for many of these applications. However, the size of a conventional permanent magnetic that is needed to provide these strong magnetic forces limits their usefulness. The structures needed to support massive conventional magnets are expensive and cumbersome. Moreover because magnetic forces fall off rapidly (with the third power of the distance for magnetic fields and with the fourth power of the distance for magnetic gradients), the magnet must be very close to the point where the magnetic force is to be applied, making the rotations and translations of the magnet to change the direction of the applied magnetic force difficult. In the special case of magnetic surgery applications, the movement of the magnet is also limited by imaging and life support equipment in the procedure room.

SUMMARY OF THE INVENTION

The present invention is a permanent magnet in which the magnetization direction varies to maximize the selected magnetic property of the magnet (e.g. field strength or gradient), and to a method of making such magnets. Generally, the magnet of the present invention comprises permanent magnets in which the magnetization direction at each point is selected to optimize the particular magnetic property. Thus in contrast to conventional permanent magnets in which the magnetization direction is uniform throughout, in the magnets of the present invention, the material at each point provides the optimum contribution to the desired magnetic property. This optimization means that a magnet of the present invention can be smaller and lighter than a conventional magnet, and yet sill provide equivalent magnetic force. This magnet is particularly useful in magnetic surgical procedures. The magnet allows smaller less cumbersome equipment to be used in to support and manipulate the magnet, and reduces the opportunity of interference with people and equipment in the procedure room.

According to the method of this invention, the magnet shape is first determined, given the physical constraints, e.g. set off distance, accommodating other structures and equipment in the vicinity of the where the magnetic will be operated; and likely manipulations required of the magnet. A permanent magnet in the selected shape is then made, in which the magnetization direction at each point is generally optimized for the selected property. This can be accomplished by providing a monolithic permanent magnet piece with a continuously varying magnetization direction, or by providing a plurality of magnetic segments, which can either have a single magnetization direction throughout, or which can themselves have continuously varying magnetization direction. In the former case, the magnetization direction is optimized for a particular point, for example the center of mass, thereby substantially approximating the optimum magnetization direction.

Thus magnets of the present invention provide improved magnetic properties for a given weight and size over conventional permanent magnet. The magnets can be manipulated by smaller and less cumbersome equipment, and due to their smaller size are less likely to interfere with, or be interfered with by persons and equipment. The method of the present invention provides magnets of the present invention.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

Figure 1:
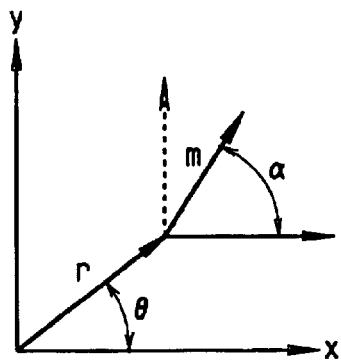
FIG. 1 is a diagram showing the relationship between a local magnetic moment m, the magnetization angle α, and the location of the moment m as given by r and θ from the origin at the application point.

The magnets of the preferred embodiments of the present invention are permanent magnets in which the magnetization direction varies by location to provide magnets that optimize a selected magnetic field property at a selected location external to the magnet. These magnets may comprise a monolithic magnet in which the magnetization direction varies smoothly and continuously so that at each location, the magnetization direction is substantially in the direction that optimizes the selected magnetic property. Alternatively, these magnets may comprise a plurality of magnet segments, each with a magnetization that is substantially in the direction that optimizes the selected magnetic field property. These magnets can be used in any application, but are particularly useful for magnetic surgical applications.

The methods of making magnets of the preferred embodiments of the present invention provide for the simple construction of optimized magnets. The methods involve the arrangement of individual magnetic dipole elements. These dipole elements may be actual microscopic magnetic domains in a material, or they may be macroscopic magnetic segments assembled to form the magnet. Using the dipole approximation, it is possible to derive formulas for the magnetization direction as a function of the position. Based upon these formulas the appropriate magnetization direction at any location can be determined. This magnetization can then be achieved by variably magnetizing a monolithic magnet, or by assembling a plurality of magnetic segments of different uniform magnetization directions.

A magnetic dipole is approximated by the formula:

$$b = \frac{\mu_0}{4\pi}\left[-\frac{m}{r^3} + \frac{3(m \cdot r)r}{r^5}\right] \quad (1)$$

where b is the magnetic field due to the elemental magnetic moment m, r is the location of the moment, and $\mu_o$ is the permeability of free space. The orientation of m for each location in the magnet is determined to maximize a selected magnetic field property at the selected operating point. The collection of N magnetic moments comprising the magnet create a source field B, that is the sum of the source fields created by each of the magnetic moments:

$$B = \sum_{i=1}^{N} b_i \quad (2)$$

In this preferred embodiment, the collection of magnetic moments that form the magnet are treated in two dimensions, i.e., in a plane. The optimization of the magnet moments which represent the local magnetization direction, will be two-dimensional, and the important elemental magnetizations will therefore lie in this chosen plane. While a full three-dimensional optimization has been carried out, the two-dimensional case is described as the preferred embodiment because magnets with constant magnetization in one direction are simpler to construct, and three-dimensional optimization yields only an incremental gain in efficiency. It is apparent to one of ordinary skill in the art that the optimization could be a three-dimensional, which although in some cases might be important, in most cases does not yield important increases in efficiency.

As discussed herein, the coordinates are chosen so that the active plane in which the moment orientations are restricted is designated the x-y plane. Then, in principle, the z-axis contains no variation in magnetization within the magnet boundaries, although it can be appreciated that boundary conditions may render this assumption slightly inaccurate depending on the restrictions or parameter optimization. Therefore, the optimal magnetization directions are easily analyzed in the plane defined by the magnetic field b and the magnetic moment m.

FIG. 1 shows the coordinate system in which the microscopic moment m, is at a magnetization angle $\alpha$, and a location given by r and $\theta$. The direction of the vector r is reversed from its usual textbook usage. This is permissible since r appears quadratically in the moment equation. It is useful in the present application, since it leads intuitively to the usage of its two-dimensional magnitude as an angular distribution of magnetized moments needed to provide required fields and/or gradients. Using the coordinate system in FIG. 1, b of equation (1) can be expressed in terms of the angles $\alpha$ and $\theta$.

$$b = \begin{Bmatrix} b_x \\ b_y \end{Bmatrix} = \frac{\mu_o m}{8\pi r^3}\begin{Bmatrix} A\cos\alpha + B\sin\alpha \\ B\cos\alpha + (2-A)\sin\alpha \end{Bmatrix} \quad (3)$$

$$\partial b_x = \begin{Bmatrix} \partial b_x/\partial x \\ \partial b_x/\partial y \end{Bmatrix} = \frac{3\mu_o m}{8\pi r^4}\begin{Bmatrix} C\cos\alpha + D\sin\alpha \\ E\cos\alpha + F\sin\alpha \end{Bmatrix} \quad (4)$$

where $$\left.\begin{aligned} A &\equiv A(\theta) = 1 + 3\cos2\theta \\ B &\equiv B(\theta) = 3\sin2\theta \end{aligned}\right\} \quad (5)$$

$$\left.\begin{aligned} C &\equiv C(\theta) = 2\sin\theta\sin2\theta - \cos\theta - 3\cos\theta\cos2\theta \\ D &\equiv D(\theta) = 3\cos\theta\sin2\theta + 2\sin\theta\cos\theta \\ E &\equiv E(\theta) = -2\cos\theta\sin2\theta - \sin\theta - 3\sin\theta\cos2\theta \\ F &\equiv F(\theta) = 2\cos\theta\cos2\theta - 3\sin\theta\sin2\theta \end{aligned}\right\} \quad (6)$$

Thus the quantities A, B, C, D, E and F are functions only of the element position angle $\theta$ relative to a coordinate system in which the elemental field b and complete field B are described. Furthermore, the quantities given by equations (3) and (4) represent the complete reduced set given that $\nabla \cdot b = 0$ and $\nabla \times b = 0$, thereby establishing that there are only four unique quantities $b_x$, the field in the x direction, $b_y$, the field in the y direction, $\partial b_x/\partial x$, the gradient in the x direction, and $\partial b_x/\partial y$, the gradient in the y direction, (assuming, as stated above, that the z components are ignored).

Co-pending U.S. patent application Ser. No. 09/497,467, filed Feb. 3, 2000, entitled An Efficient Magnet System for Magnetically-Assisted Surgery, incorporated herein by reference, details one embodiment in which the completed magnet is operated so that the procedure point in a patient is on the central x-y plane.

Figure 2:
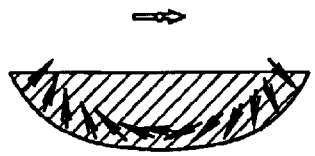
FIG. 2 is a top plan view of a first embodiment of a magnet, constructed according to the principles of this invention, optimized to provide a strong, transverse field at a selected application point spaced from the magnet face.
Figure 3:
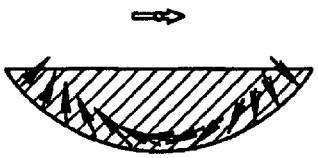
FIG. 3 is a top plan view of a second embodiment of a magnet constructed according to the principles of this invention, in which the magnet field was restricted during design to provide a transverse field at a selected application point spaced from the magnet face.
Figure 4:
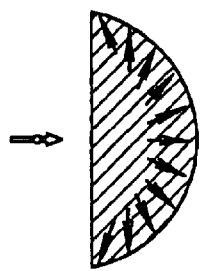
FIG. 4 is a top plan view of a third embodiment of a magnet, constructed according to the principles of this invention, optimized to provide a strong, forward field at a selected pointed spaced from the magnet face.
Figure 5:
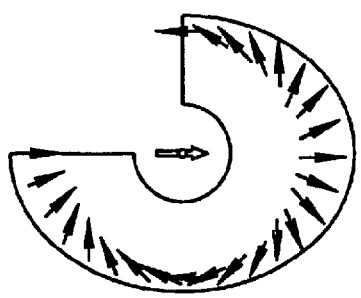
FIG. 5 is a top plan view of a fourth embodiment of a magnet constructed according to the principles of this invention, illustrating how the restriction of field direction permits asymmetry in magnet construction.

The essence of the methods described herein is to select the desired magnetic field properties of the completed magnet, and apply the requisite implied conditions to the individual elemental moments. For example, if a strong, flat, transverse, central field region is needed for the operating region of a magnet, the individual elemental moments (at angle $\alpha$) can be aligned relative to their locations (i.e., as specified by angle $\theta$ in the plane) so as to produce optimal contributions to that type of field. This is a unique vector type of "focusing" to accomplish a desired field projection for each element of the magnet, adding up to an optimum for the complete magnet. As described in more detail below, the first step in development of a magnet is to calculate the relationship between $\alpha$ and $\theta$ for the selected magnetic field property and selected location, for the magnet. In the case of a predominantly transverse field over the operating center region of the magnet, one requisite implied condition would be to set $b_y$ equal to zero in equation (3) above. FIGS. 2 and 4 show alternative magnet constructions for optimizing the magnetic field along the x-direction. In FIG. 2 the field is parallel to the magnet face. In FIG. 4, the field is perpendicular to the magnet face. In the case of the restricted field magnets (shown in FIGS. 3 and 5) the magnets provide strong fields in a given direction by setting perpendicular components to zero at the outset. In the case of optimized field magnets (shown in FIGS. 2 and 4) the magnets provide the mathematical optimum filed strength. The restricted field magnets, automatically achieves the desired field direction, irrespective of magnet shape or symmetry (as illustrated by FIG. 5). The optimal field magnet provides the optimal field strength in the desired direction, for a given size, but requires symmetric retention of elements to preserve field direction.

In another application, the requirement may be for a gradient that is zero except in a selected direction in a selected region spaced from the magnet. The magnetic field gradient is a tensor, so in two-dimensions, two such cases can exist mathematically, for $\partial b_x/\partial x=0$ or for $\partial b_x/\partial y=0$, by the use of equation (4) above. ($\partial b_y/\partial x = \partial b_x/\partial y$ from $\nabla \times b = 0$.) Clearly, a number of magnet shapes could be used with this restricted case.

In still another application, the requirement may be for the optimization of the magnetic field gradients in some region. And still another application, the requirement may be for the field-gradient products to be optimized. This last case would be useful for the pulling of permeable materials or objects in some particular direction, while orienting them in the same or a different direction. Five major categories of these restrictions and optimizations are discussed below. One of ordinary skill in the art could use similar methods for other cases.

Once the optimal magnet shape and the magnetization direction for a given position are determined, a permanent magnet can be fabricated from a permanent magnetic material, such as a neodymium-boron-iron (Nd—B—Fe) material, of the appropriate shape can be magnetized in the appropriate directions, or a magnet can be assembled from a plurality if magnetic segments, with the proper shape and magnetization direction.

Specifically, the five major categories of cases employ two different procedures: restriction and optimization, although similar results can sometimes be achieved by either procedure. The two procedures differ, organizationally, in the use either of restriction of an undesired property, or the optimization of a desired property. The details of element selection at the end to achieve a final complete magnet will be motivated somewhat differently in the two procedures.

Cases A and B first restrict components of certain magnetic field properties so as to a priori provide the directions needed for the desired properties. The case will then, at the end, use material removal to make the magnet as small and light as possible while achieving required strengths of the desired quantities at the desired location.

Alternatively, cases C, D and E will first optimize (maximize) the desired quantities, and at the end remove material to simultaneously make the magnet smaller and to rid the field of undesired "off-direction" components of the desired quantity, since the procedure will not have automatically removed them. Clearly, attention to symmetry is important.

A. Restricted Field Case

This case first restricts a magnetic field property, uses equations to arrive at a prototype magnet shape, and then uses judicious material removal to optimize the desired quantity in conjunction with achieving the smallest and lightest magnet, typically using an iterative or trial and error method. This case does not use a formal optimization procedure.

In this case, one component of the magnetic field of the element is zeroed at a distance from the magnet. This restricted case is useful in that the magnet may be composed of segments that do not need to be balanced (i.e., symmetry need not be reflected in the magnet's material removal, or design) to ensure that one component of the field remains zeroed.

Figure 6:
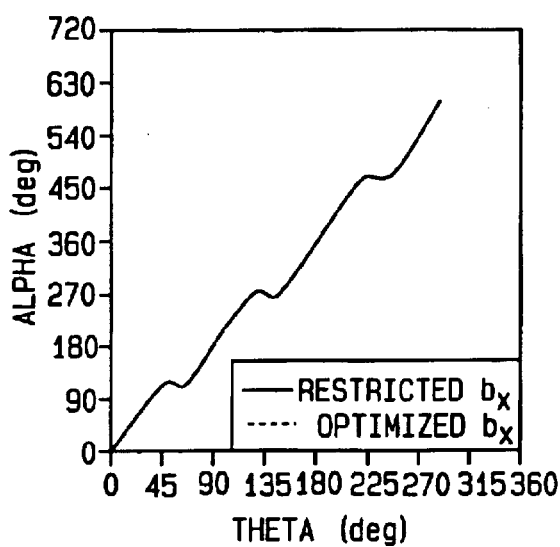
FIG. 6 is a graph of magnetization angle α versus position angle θ for restricted $b_x$ (i.e., $b_y=0$) (the magnet shown in FIG. 3), and for the optimized of $b_x$ (the magnet shown in FIG. 2)
Figure 7:
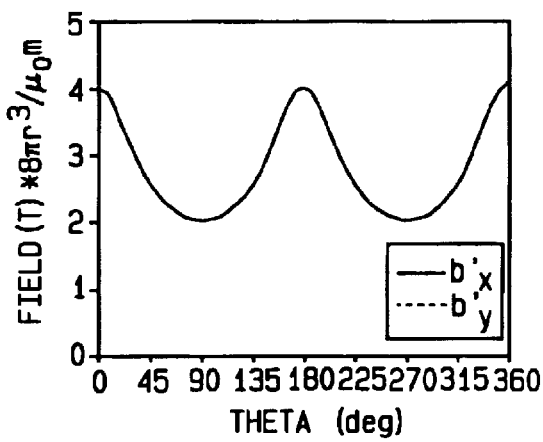
FIG. 7 is a graph of the scaled magnetic field component in the x direction ($b'_x$) versus position angle θ of the element for a restricted field magnetization case ($b_y=0$), the scaled magnet field component in the y direction ($b'_y$) being zero.
Figure 8:
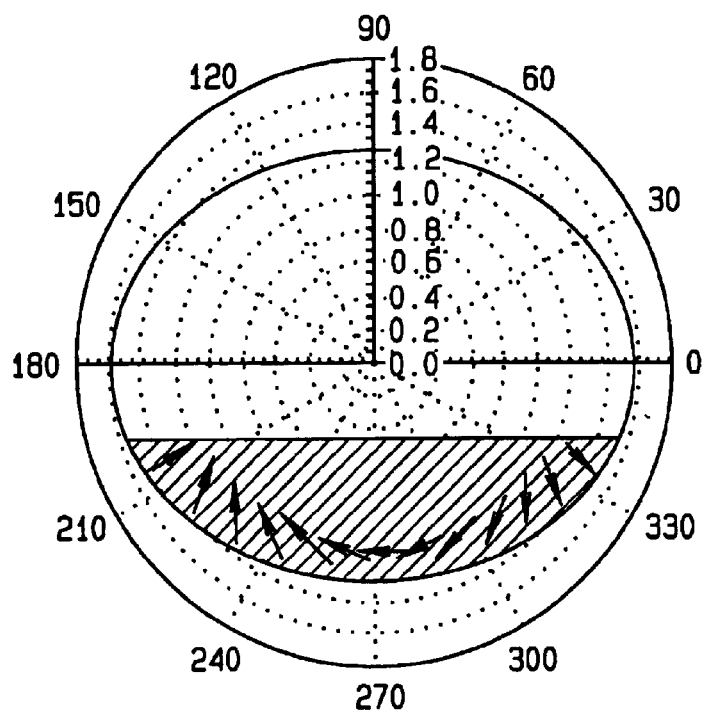
FIG. 8 is a constant contribution curve, i.e., the curve representing the positions where a properly aligned magnetic moment would contribute equally to the field in the x direction at the origin, (i.e., an angular distribution curve r vs. θ as a polar plot) for the restricted field magnetization curve ($b_y=0$))

The procedure here will be first to develop equations which relate the magnetization angle $\alpha$ to the position angle $\theta$ for a particular element so that it will contribute a magnetic field only in the x direction, i.e. so $b_y=0$, for some point of interest in the operating region. This can be thought of as a conditional requirement on each particular element, to be used later in the assembly of elements for the magnet. This might, for example, be a case where a transverse field was needed in the patient procedure volume. FIGS. 6, 7, and 8 will be used to depict, respectively and as described above, the consequences of this restriction on 1) the magnetization angle-position angle relationship, 2) the relative magnetic field component contributions vs. position angle $\theta$ at an implicit but correctly scaled distance r, and 3) a polar plot of the distance r at which the given reference field strength is reached in the x-y plane.

Setting $b_y=0$, we find that $$\tan\alpha = \frac{B}{A-2} \qquad (7)$$

relates the magnetization angle $\alpha$ to the element position angle $\theta$ (implicitly through A and B). This is depicted as the solid line in FIG. 3. From symmetry, the case $b_x=0$ can be seen by extrapolation. FIG. 6 contains the information which is needed to keep track of (in the computer) the magnetization directions $\alpha$ in the "shape" plot or "angular distribution" plot, FIG. 8 below, which is used to determine the final magnet shape. FIG. 7 portrays the change in the magnetic field contributions of the elements due to their varying magnetization directions (as a consequence of varying $\theta$) where the plotted field is scaled so that $$b' = \left(\frac{8\pi r^3}{\mu_o m}\right) b.$$

It also follows that for constant contributions of $b_x$, the desired shape of the magnet is given by solving the x-component of equation (3) for r:

$$r = \left(\frac{\mu_o m}{8\pi b_x}\right)^{1/3} (A\cos\alpha + B\sin\alpha)^{1/3} \qquad (8)$$

for which $\theta$, again, is implicit in A and B. This is shown by the polar plot of FIG. 5 (i.e., r versus $\theta$) where the radial component is scaled by the quantity $$\left(\frac{8\pi b_x}{\mu_o m}\right)^{1/3}.$$

A few of the directions $\alpha$ (implicit in $r(\theta)$) are shown by the arrows around the $r(\theta)$ curve. The magnet shown in FIG. 3 is derived from this restricted field case.

In summary, the magnet shape and ideal magnetization distribution is determined in the x-y plane from FIG. 8, which represents a locus of the planar value of r at which a reference value of $b_x$ is achieved.

B. Restricted Gradient Case

Similar in overall method to the restricted field case, this case, in addition to practically restricting a different quantity, is useful in that the magnet may then be composed of segments that do not require symmetry in their design to remove the influence of undesirable gradient terms at the point r. For the choice of gradient direction null $\partial b_x/\partial x=0$ we find that $$\tan\alpha = -\frac{C}{D} \qquad (9)$$

and for $\partial b_x/\partial y=0$ it follows that $$\tan\alpha = -\frac{E}{F} \qquad (10)$$

Figure 9:
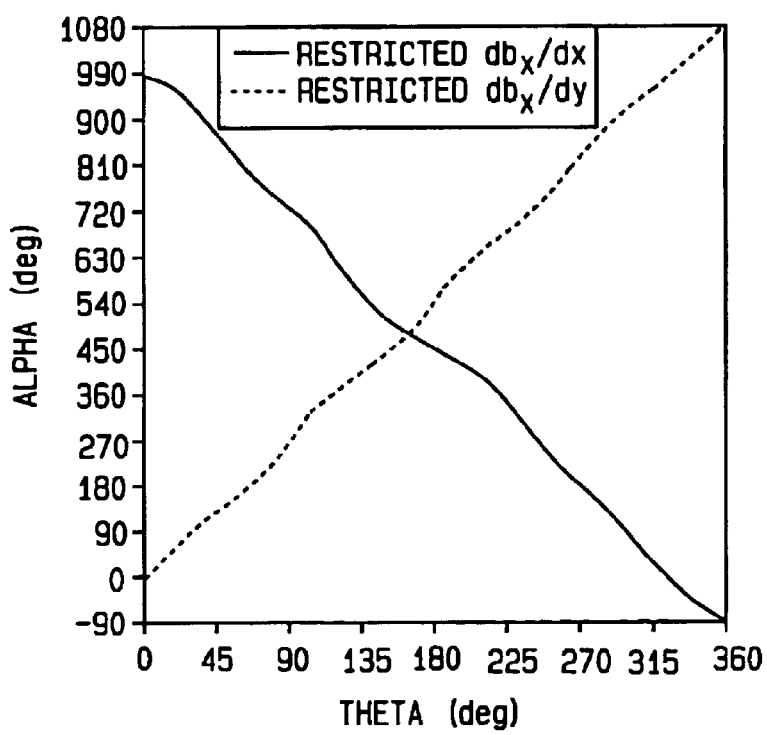
FIG. 9 is a graph of magnetization angle α versus position angle θ for the restricted gradient ($\partial b_x/\partial x=0$) and for the restricted gradient ($\partial b_x/\partial y=0$)
Figure 10:
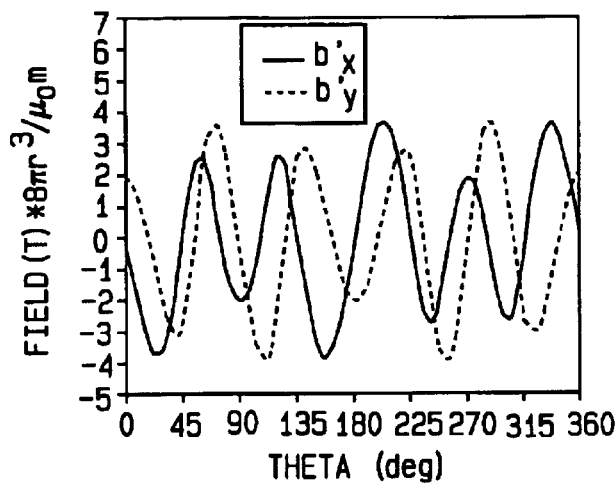
FIG. 10 is a graph of the scaled magnetic field components in the x direction ($b'_x$) and in the y direction ($b'_y$) of the contributing element versus position angle θ of the element for the restricted transverse field gradient in the axial direction case ($\partial b_x/\partial x=0$)
Figure 11:
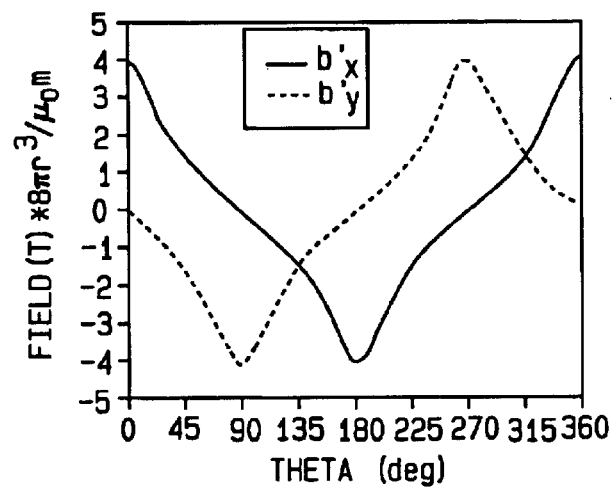
FIG. 11 is a graph of the scaled magnetic field components in the x direction ($b'_x$) and in the y direction ($b'_y$) of the contributing element versus position angle θ of the element for the restricted transverse field gradient in the transverse direction case ($\partial b_x/\partial y=0$)

FIG. 9 depicts the results of equations (9) and (10), showing $\alpha$ versus $\theta$ explicitly in the two sub-cases. FIGS. 10 and 11 plot the relationship of the scaled magnetic field contributions to θ for the two cases ∂b$_x$/∂x=0 and ∂b$_x$/∂y=0, respectively. In FIG. 9 there are now two α-θ relationships, corresponding to the two directions of gradient restriction. It is notable, and relevant to final magnet design, that while θ was double-valued in α for the restricted field condition, it is now triple-valued in α in each of the gradients not restricted to zero. The two curves in FIG. 10 for the scaled field component ( b$_x$' and b$_y$') contributions, both of which now survive, oscillate with θ but are 90 degrees out of phase. In FIG. 11 the scaled magnetic field components contributions again oscillate out of phase, but with only a single cycle in 360 degrees of θ.

Figure 12:
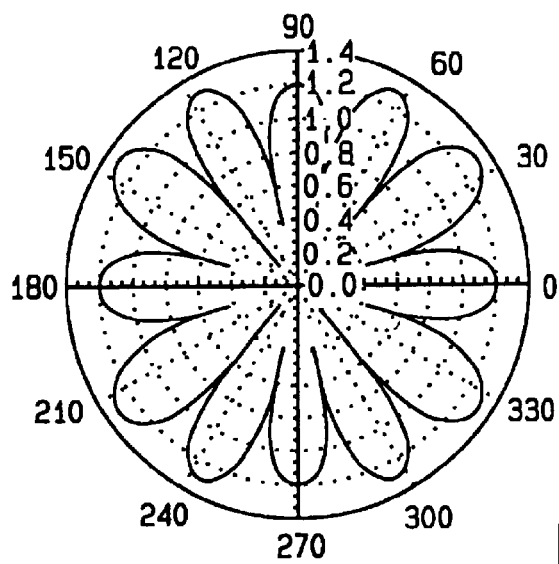
FIG. 12 is a constant contribution curve, i.e., the curve representing the positions where a properly aligned magnetic moment would contribute equally to the axial gradient component of the transverse field (i.e., the field in the x direction) at the origin, (i.e., an angular distribution curve r vs. θ as a polar plot) for the restricted gradient magnetization case ($\partial b_x/\partial x=0$)

Given a constant gradient component a ∂b$_x$/∂y, the polar plots for the radial component r for which ∂b$_x$/∂x=0 are shown in FIG. 12 where $$r = \left(\left[\frac{3\mu_o m}{8\pi(\partial b_x/\partial y)}\right]\right)^{1/4} (E\cos\alpha + F\sin\alpha)^{1/4} \quad (11)$$

Figure 13:
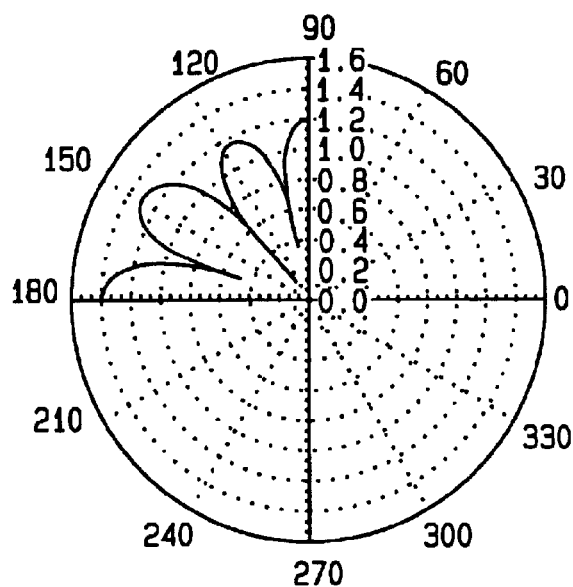
FIG. 13 is a constant contribution curve, i.e., the curve representing the positions where a properly aligned magnetic moment would contribute equally to the transverse gradient component of the transverse field (i.e., the field in the x direction) at the origin, (i.e., an angular distribution curve r vs. θ as a polar plot) for the restricted gradient magnetization case ($\partial b_x/\partial y=0$)

Likewise, a constant ∂b$_x$/∂x for which ∂b$_x$/∂y=0 yields FIG. 13 where now $$r = \left(\left[\frac{3\mu_o m}{8\pi(\partial b_x/\partial x)}\right]\right)^{1/4} (C\cos\alpha + D\sin\alpha)^{1/4} \quad (12)$$

In these restricted cases, the correct $1/r^4$ dependence of the gradient is retained so that the appropriate magnitudes are preserved. The multi-lobed shape curves (angular distribution curves) require more care in the use of symmetries, etc. in the design of the complete magnet, e.g. the choice of where to remove material.

C. Maximized Field Cases

Instead of restricting a field or gradient component at some selected focal point (operating region), it may be more useful to use an alternative, formal optimization method to achieve a similar but better result. Here the distributions are calculated for element orientations which are formally optimized to maximize a field component. For example, it will optimize (maximize) a field component to replace the a priori restricting of an undesired component as was the case in case A. The resulting optimized magnet shapes can be seen by comparing the magnet in FIG. 2 (optimized) and FIG. 3 (restricted). In this new case, we wish to relate α to θ for the magnetic moments to be oriented in such a manner as to contribute maximally to either b$_x$ or b$_y$, depending on the desired direction of the field relative to the magnet face. Given that the field components are analogous if θ sweeps from 0 to 2π, ∂b$_x$/∂α=0 yields:

$$\tan\alpha = \frac{B}{A}. \quad (13)$$

Figure 14:
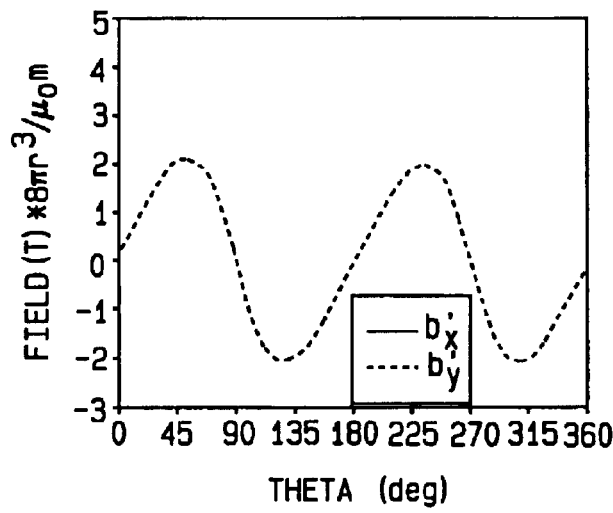
FIG. 14 is a graph of the scaled magnetic field component in the x direction ($b'_x$) and in the y direction ($b'_y$) of the contributing element versus position angle θ of the element for the optimized field magnetization case ($b_x$ maximized) (e.g. for the magnet shown in FIG. 2)
Figure 15:
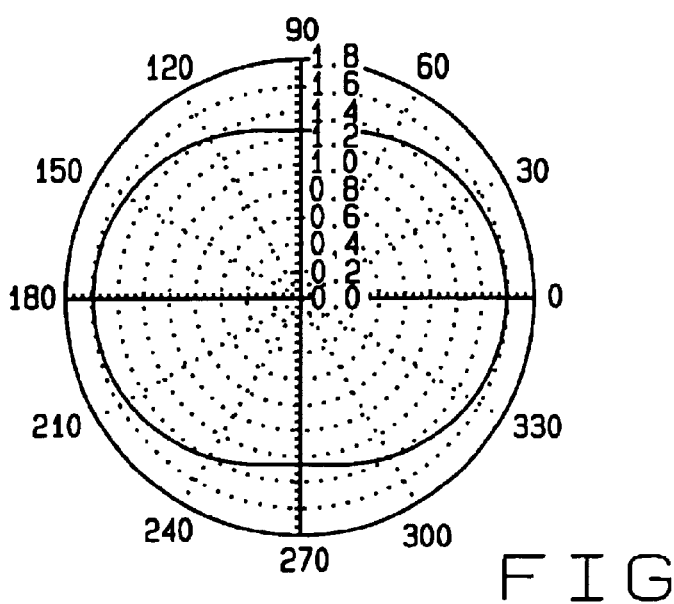
FIG. 15 is a constant contribution curve, i.e., the curve representing the positions where a properly aligned magnetic moment would contribute equally to the field in the x direction at the origin, (i.e., an angular distribution curve r vs. θ as polar plot) for the optimized field magnetization case ($b_x$ maximized)

The relationship between α and θ for this optimized field case is shown in dashed lines in FIG. 6. FIG. 14 details the relationship of the magnetic field component contributions to θ. Obviously, care must be taken in the design of the complete magnet by judicious choice of symmetry to ensure the removal of the y-component of the field which now is not automatically excluded at the start. The nature of r is identical in form to that expressed in equation (8). However, since the relationship between α and θ is now given by equation (13) rather than by equation (7), we see that r versus θ now takes the simple form of FIG. 15, which is different from the form resulting from the restricted field case shown in FIG. 8. It should also be noted that for a maximum to exist, $\partial^2 b_x/\partial\alpha^2 < 0$ which results in the requirement that b$_x$>0, an obvious condition.

Thus, the new result yields the magnet shape shown in FIG. 2, as opposed to the shape shown in FIG. 3 for the restricted field case, to arrive at a particular field strength for a strictly transverse field parallel to the magnet face at some given distance. It is apparent that the new method yields a smaller optimal magnet cross section, and a lighter magnet in this particular type of design problem.

D. Optimized Gradient Case

Here the overall procedure parallels that of case C. But now the gradient components, not the field components, are formally maximized, and the material removal is used (with symmetry considerations) at the end to achieve the desired gradient directions.

Figure 16:
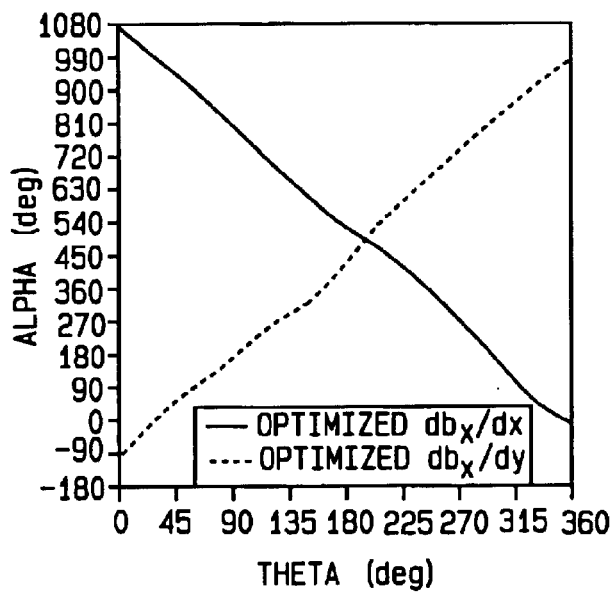
FIG. 16 is graph of magnetization angle α versus position angle θ for optimized gradient component ($\partial b_x/\partial_x$ optimized with respect to α), and for optimized gradient component ($\partial b_x/\partial y$ optimized with respect to α)
Figure 17:
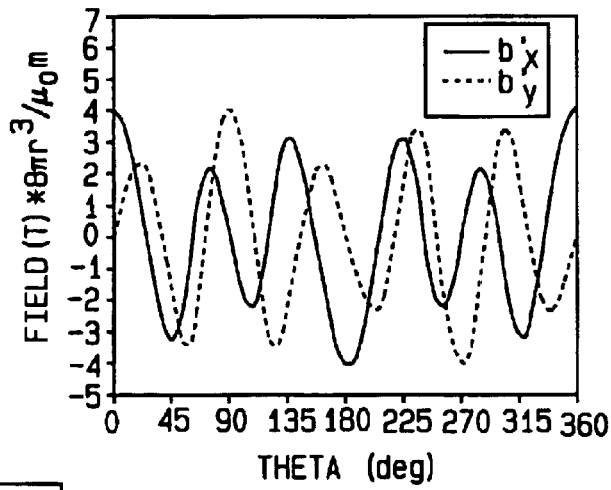
FIG. 17 is a graph of the scaled magnetic field components in the x direction ($b'_x$) and in the y direction ($b'_y$) of the contributing element versus position angle θ of the element for the optimized transverse gradient of the transverse field ($\partial b_x/\partial x$ optimized with respect to α)
Figure 18:
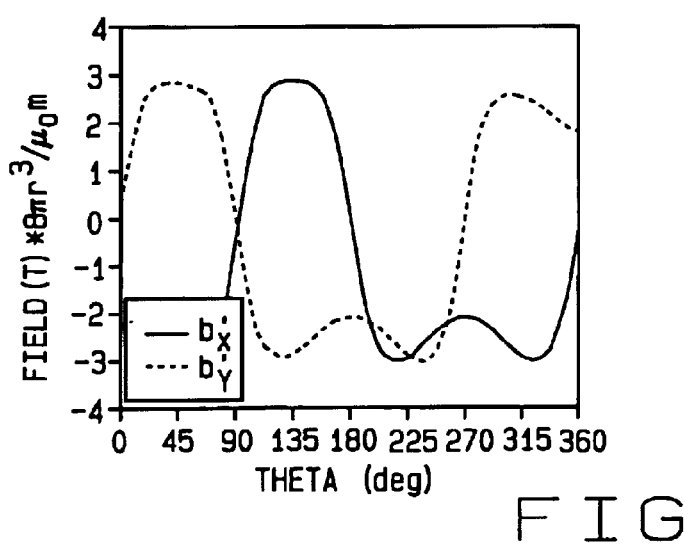
FIG. 18 is a graph of the scaled magnetic field components in the x direction ($b'_x$) and in the y direction ($b'_y$) versus position angle θ for the optimized axial gradient of the transverse field ($\partial b_x/\partial y$ optimized with respect to α)
Figure 19:
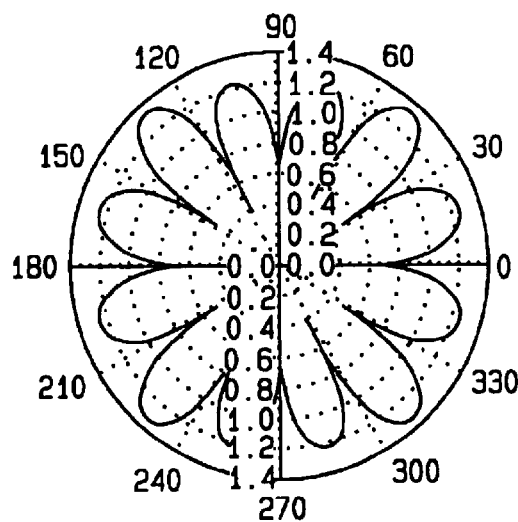
FIG. 19 is a constant contribution curve, i.e., the curve representing the positions where a properly aligned magnetic moment would contribute equally to the optimized transverse gradient of the transverse field (i.e., the field in the x direction) at the origin, (i.e., an angular distribution curve r vs. θ as polar plot) for the optimized gradient magnetization case ($\partial b_x/\partial x$ optimized)
Figure 20:
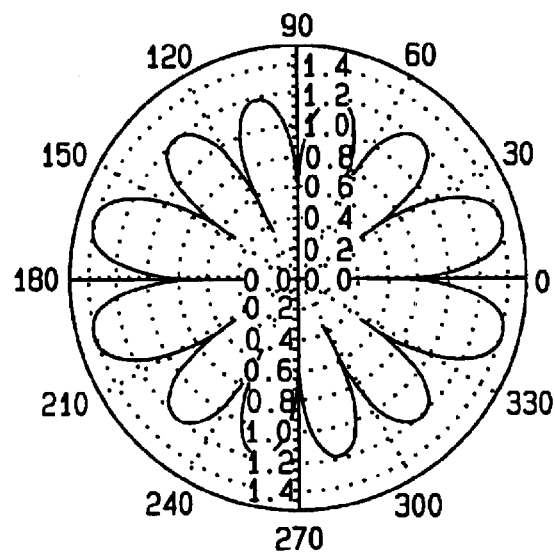
FIG. 20 is a constant contribution curve, i.e., the curve representing the positions where a properly aligned magnetic moment would contribute equally to the optimized axial gradient of the transverse field (i.e., the field in the x direction) at the origin, (i.e., an angular distribution curve r vs. θ as a polar plot) for the optimized gradient magnetization case ($\partial_x/\partial y$ optimized)

As in the procedures above, we relate α to θ so that the moment of the element is oriented in a manner to contribute maximally to the required quantity, except that here that quantity is either $$\partial b_x/\partial x \text{ or } \partial b_x/\partial y. \text{ For } \frac{\partial}{\partial\alpha}\left(\frac{\partial b_x}{\partial x}\right) = 0$$

we calculate $$\tan\alpha = \frac{D}{C} \quad (14)$$

which yields the α-θ relationship shown in solid lines in FIG. 16. The magnetic field component contribution is depicted in FIG. 17 and the variable r takes the form of equation (12), but with the new implicit α-θ relationship changing the result. That is plotted in FIG. 19.

$$\text{For } \frac{\partial}{\partial\alpha}\left(\frac{\partial b_x}{\partial y}\right) = 0: \quad (15)$$

$$\tan\alpha = \frac{F}{E}$$

which yields the α-θ relationship shown in dashed lines in FIG. 16. Now FIG. 18 plots the magnetic fields and the behavior of r is in the form of equation (11) and depicted in FIG. 20. As discussed above, the ignored gradients and field components must be examined in determining less important material removal in the magnet's design, depending on the application of the magnet.

E. Maximized Field-Gradient Product Case

Again, as in cases C and D, the overall procedure is to formally maximize a desired quantity and finally to use symmetry conditions on material removal to achieve the desired magnetic field property of interest.

It is often of interest to provide a pulling force on a permeable material or medium. A good quantity in most cases for evaluating such a force is the field-gradient product. Therefore in this final major case, it is desired to maximize the quantities $$b_x \frac{\partial b_x}{\partial y} \text{ and } b_x \frac{\partial b_x}{\partial x}$$

which represent the only unique components of the field-gradient product. All other cases for the field-gradient product follow from ∇·b=0 and ∇×b=0. From equations (3) and (4) we rewrite the field-gradient product in the form of $$b_x \frac{\partial b_x}{\partial y} = \quad (16)$$

$$\frac{3}{2r^7}\left(\frac{\mu_o m}{8\pi}\right)^2 [(AE+BF) + (AE-BF)\cos 2\alpha + (BE+AF)\sin 2\alpha]$$

$$b_x \frac{\partial b_x}{\partial x} = \quad (17)$$

$$\frac{3}{2r^7}\left(\frac{\mu_o m}{8\pi}\right)^2 [(AC+BD) + (AC-BD)\cos 2\alpha + (BC+AD)\sin 2\alpha]$$

Thus for $$\frac{\partial}{\partial \alpha}\left(b_x \frac{\partial b_x}{\partial y}\right) = 0,$$

we find that $$\tan 2\alpha = \frac{BE+AF}{AE-BF} \quad (18)$$

and for $$\frac{\partial}{\partial \alpha}\left(b_x \frac{\partial b_x}{\partial x}\right) = 0,$$

the relationship between α and θ becomes $$\tan 2\alpha = \frac{BC+AD}{AC-BD} \quad (19)$$

where the condition for a maximum to exists for both equations (16) and (17) is that $\tan^2 2\alpha \geq -1$.

Figure 21:
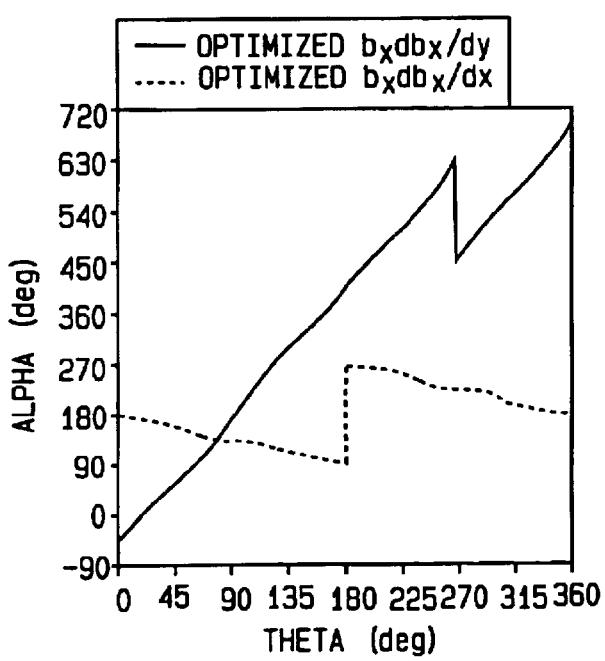
FIG. 21 is graph of magnetization angle α versus position angle θ for optimized field-gradient product components ($b_x(\partial b_x/\partial x)$ optimized) and ($b_x(\partial b_x/\partial y)$ optimized)
Figure 22:
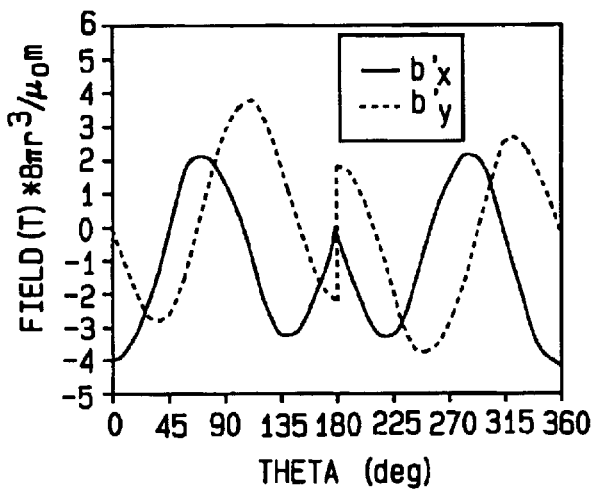
FIG. 22 is a graph of the scaled magnetic field components in the x direction ($b'_x$) and in the y direction ($b'_y$) of the contributing element versus position angle θ for the element for optimized field-gradient product magnetization case ($b_x(\partial b_x/\partial x)$ optimized)
Figure 23:
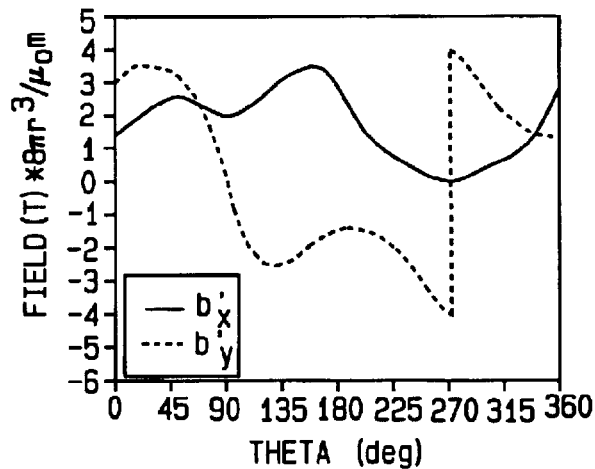
FIG. 23 is a graph of the scaled magnetic field components in the x direction ($b'_x$) and in the y direction ($b'_y$) of the contributing element versus position angle θ for optimized field-gradient product magnetization case ($b_x(\partial b_x/\partial y)$ maximized)

The relationship between α and θ, from equations (18) and (19), is shown in FIG. 21 in solid liens for $b_x db_x/dy$ and in dashed lines for $b_x db_x d_x$, and the field distribution plots for the two sub-cases are in FIGS. 22 ($b_x db_x/dy$) and 23 ($b_x db_x/dx$). The two-dimensional r(θ) curves detailed in equations (20) and (21) follow from (16) and (17), respectively:

$$r = \left[\frac{3}{2b_x(\partial b_x/\partial y)}\left(\frac{\mu_o m}{8\pi}\right)^2\right]^{1/7} [(AE+BF) + (AE-BF)\cos 2\alpha + (BE+AF)\sin 2\alpha]^{1/7} \quad (20)$$

$$r = \left[\frac{3}{2b_x(\partial b_x/\partial x)}\left(\frac{\mu_o m}{8\pi}\right)^2\right]^{1/7} [(AC+BD) + (AC-BD)\cos 2\alpha + (BC+AD)\sin 2\alpha]^{1/7} \quad (21)$$

Figure 24:
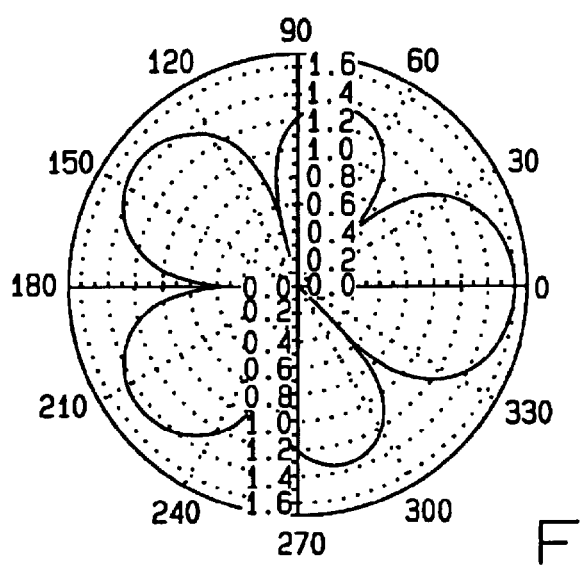
FIG. 24 is a constant contribution curve, i.e., the curve representing the positions where a properly aligned magnetic moment would contribute equally to the optimized field gradient product at the origin, (i.e., an angular distribution curve r vs. θ as a polar plot) for the optimized gradient magnetization case ($b_x(\partial b_x/\partial x)$ optimized)
Figure 25:
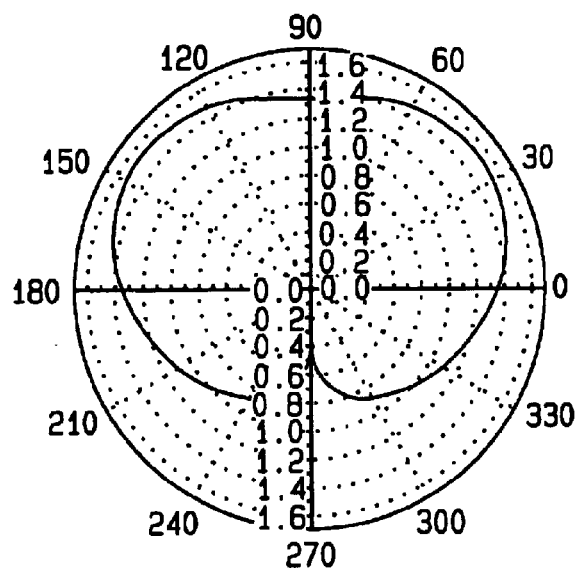
FIG. 25 is a constant contribution curve, i.e., the curve representing the positions where a properly aligned magnetic moment would contribute equally to the optimized field gradient product at the origin, (i.e., an angular distribution curve r vs. θ as a polar plot) for the optimized gradient magnetization case [$b_x(\partial b_x/\partial y)$ maximized]

These are shown as polar plots in FIGS. 24 and 25, respectively. Care must be paid to the symmetry of the magnetic field components and gradients in the magnet's design if pure field-gradient terms are to be generated (e.g., for $b_x(\partial b_x/\partial y)$ maximized with $b_y=0$ and $\partial b_x/\partial x=0$).

Operation

In designing a magnet in accordance with the principles of this invention, one would first generally select the desired shape of the magnet. This is most conveniently done with two dimensional optimization by using the curves of constant contribution for the magnetic field property that is to be optimized or restricted, to give the shape in two dimensions, i.e., in the x-y plane. The height in the z-axis can then be selected based on the available space, desired weight, and required field strength. Once the shape of the magnet is generally determined, the magnetization direction at each location is then determined. For optimization in two dimensions, the relations between the magnetization direction angle α verses the position angle θ, discussed above can be use to determine the proper magnetization angle at each location.

In the case of a monolithic magnetic, a blank of permanent magnetic material can be made in the desired shape and magnetized so that the magnetization direction varies smoothly and continuously in the x-y plane in accordance with the proper magnetization direction determined by the appropriate relation between the magnetization direction angle α verses the position angle. As noted above, in most cases the magnetization need not vary in three dimensions, and thus the direction of magnetizations vary only in the x-y plane. This means that the magnet can be made of a single monolithic block or a plurality of similar permanent magnet slabs stacked in the non-critical (i.e., the z direction).

In the case of a multi-segmented magnet, a plurality of permanent magnet segments are assembled to conform substantially to the desired shape. The magnetization direction of each segment is selected so that the magnetization direction within the segment conforms substantially to the proper magnetization direction. Ideally the magnetization would vary within the segment to conform to the proper magnetization direction that satisfied the optimization/restriction criteria for the desired magnetic field property. However, achieving the ideal is technically difficult and expensive, and with judicious selection of the sizes and shapes of the permanent magnet segments makes this unnecessary. A single uniform magnetization direction can usually be selected for each segment that satisfactorily approximates the ideal magnetization direction distribution. For example, the magnetization direction for a segment could be selected to be the ideal direction at the location of the center of mass of the segment. The magnetization direction for the segment could alternatively be selected to be the ideal direction at the location of the magnetic center of the segment, (i.e. the location of at which a single magnet dipole of equivalent strength could replace the segment), or the material in the segment could be otherwise weighted (for example, inversely to the cube of the distance between each point in the segment and the selected point), to provide the appropriate point for in the segment to determine the proper magnetization direction to apply to the entire segment.

The monolithic magnets in accordance with this invention ideally would have cross-sectional shapes in the x-y plane corresponding to the shape of the constant contribution for the particular magnetic field property being optimized or restricted. This provides the most efficient magnet for the volume and weight. Thus, at least some of the surfaces of the magnets of this invention, and in particular the surfaces that face away from the selected point of application of the optimized restricted magnetic field property, conform to the surface of constant contribution. However, as a practical matter it can be difficult to form magnetic material into this shapes, and in many cases where volume and weight are not critical, it is not necessary that the magnet have this shape. As long as the magnetization direction is properly oriented throughout the magnet, the additional material does not impair the optimized/restricted magnetic field property, it merely makes the magnet larger and heavier than necessary.

Where size and/or weight of the magnet is critical, then the constant contribution curves provide guidance of where to remove material with the least impact on the magnet field properties. More specifically for a given constant contribution surface, it is always more efficient to remove material outside the surface before removing material inside the surface, even if the material outside the surface is closer to the selected point than other material inside the surface. Thus, for convenience magnets can be made in square or rectangular blocks that either approximate the optimal curved surfaces, or that are machined to approximate the optimal curved surfaces.

Figure 27A:
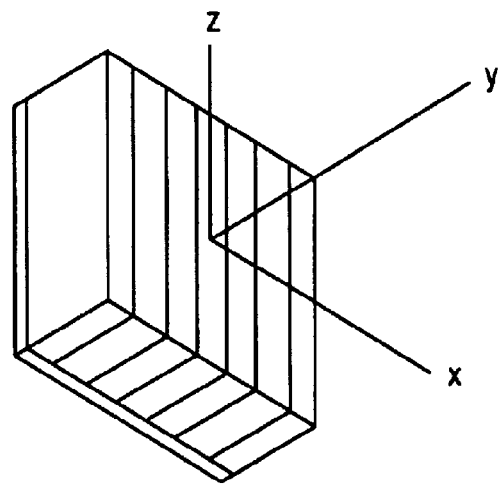
FIG. 27A is a front perspective view of an alternate construction of a magnet constructed from a plurality of permanent magnet segments, according to the principles of this invention.
Figure 27B:
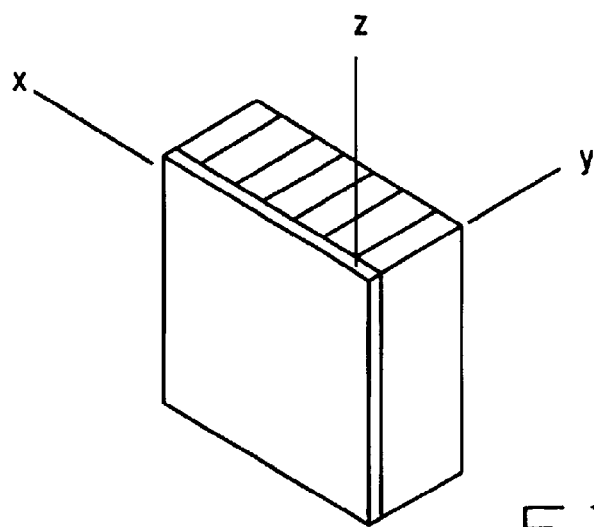
FIG. 27B is a rear perspective view of the magnet shown in FIG. 27A.
Figure 26B:
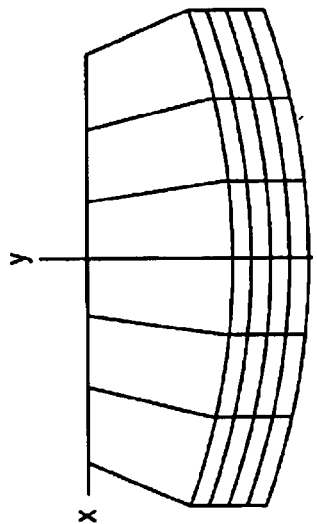
FIG. 26B is top plan view of the magnet shown in FIG. 26A.
Figure 26D:
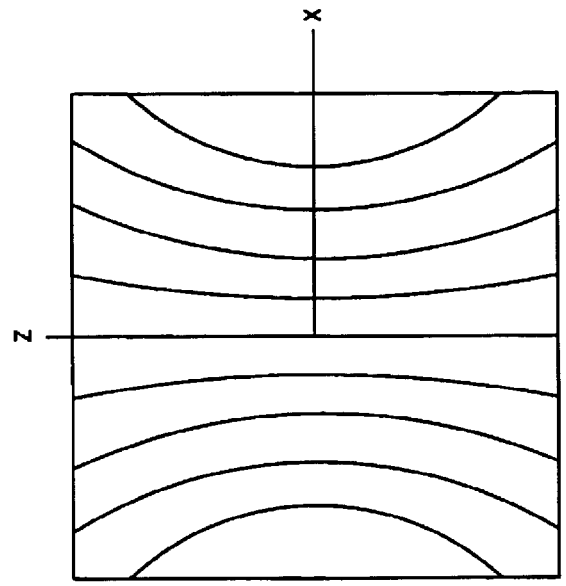
FIG. 26D is a front elevation view of the magnet shown in FIG. 26A.
Figure 26A:
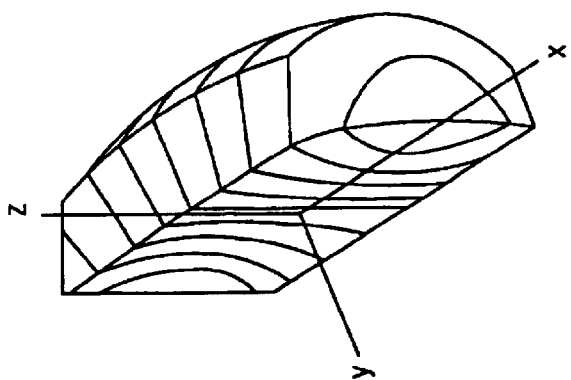
FIG. 26A is a perspective view of a magnet constructed from a plurality of permanent magnetic segments, according to the principles of this invention.
Figure 26C:
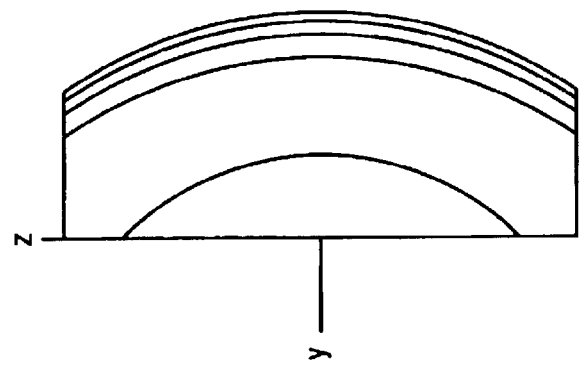
FIG. 26C is a side elevation view of the magnet shown in FIG. 26A.

For example, in making a magnet that maximizes the transverse field, an appropriate curve of constant contribution for the magnet size and strength is used. See FIG. 8. The setoff distance between the magnet and the selected operating point is selected, and the cross section of the magnet in the x-y plane is then determined. The properties of the magnet field that would be created by such a magnet can be calculated to determine if the magnet is the appropriate size. If the properties are larger than required, a smaller magnet can be selected. if the properties are smaller than required, a larger magnet can be selected. The magnet can then be completed by providing a monolithic block or permanent magnet material of the selected cross section, or a plurality of slabs of the selected cross-section, and magnetizing the block or the slabs in the direction α in the x-y plane determined by the position angle θ, given by relation between α and θ for the desired optimization or restriction of the magnetic field properties. Of course, rather than using a monolithic block, or a plurality of slabs stacked in the z direction, the magnets can be assembled from a plurality of segments. The segments can be shaped to form the magnetic of the desired shape (see FIGS. 26A–D), or where the size and weight are not important, they can simply be rectangular prisms, which as easier to work with (see FIGS. 27A and B). Each segment has the appropriate magnetization direction α in the x-y plane for the location of the segment θ. Of course, for ease of manufacture, the magnet can be made with rectangular segments as shown in FIG. 27, and machined or otherwise shaped to the optimal shape, such as that shown in FIG. 26.

What is claimed is:

1. A method of performing a medical procedure using magnet to project a magnetic field into a patient to control a magnetic medical element inside the patient, where the magnet comprises a plurality of permanent magnet segments, the magnetization direction of each permanent magnet segment varying in three dimensions with respect to each segment's assembled location so that the magnetization direction of each permanent magnet segment is in the direction that substantially optimizes the strength of the externally projected magnetic field at a selected point.

2. A permanent magnet in which the magnetization direction varies with location to optimize the magnetic field at an externally selected point in a selected direction, the magnet comprising a plurality of permanent magnet segments, the magnetization direction of each permanent magnet segment varying in three dimensions with respect to each segment's assembled location so that the magnetization direction of each permanent magnet segment is in the direction that substantially optimizes the magnetic field strength of the externally projecting at the selected point in the selected direction.

3. The permanent magnet according to claim 2 wherein at least a portion of the surface of the magnet conforms to a surface of constant contribution to the desired magnetic field at the selected location point.

4. The permanent magnet according to claim 3 wherein the direction of magnetization throughout each permanent magnet segment is constant.

5. The permanent magnet according to claim 4 wherein the direction of magnetization throughout each permanent magnet segment is the direction which, at the center of mass of the segment, provides the maximum contribution to the desired property optimizing the field.

6. The permanent magnet according to claim 4 direction of magnetization throughout each permanent magnet segment is the direction which, at the effective magnet center, provides the maximum contribution to the desired property optimizing the field.

7. The permanent magnet according to claim 4 wherein the size and position of the permanent magnet segments is selected so that the difference in the direction of magnetization direction between adjacent magnet segments is less than about 45°.

8. The permanent magnet according to claim 7 wherein the size and position of the permanent magnet segments is selected so that the difference in the direction of magnetization direction between adjacent magnet segments is less than about 30°.

9. The permanent magnet according to claim 3 wherein the magnetization direction throughout each permanent magnet segment is not constant.

10. A permanent magnet in which the magnetization direction varies with location to optimize a the magnetic field at an externally selected point in a selected direction, the magnet comprising: a plurality of permanent magnet segments, the magnetization direction of each permanent magnet segment varying in two dimensions with respect to each segment's assembled location so that the magnetization direction of each permanent magnet segment is in the direction that substantially optimizes the strength of the externally projecting magnetic field at the selected point in the selected direction.

11. The permanent magnet according to claim 10 wherein at least a portion of the surface of the magnet conforms to a surface of constant contribution to the desired magnetic field at the selected location point.

12. The permanent magnet according to claim 10 wherein the direction of magnetization throughout each permanent magnet segment is constant.

13. The permanent magnet according to claim 12 wherein the direction of magnetization throughout each permanent magnet segment is the direction which, at the center of mass of the segment, provides the maximum contribution to the desired property optimizing the field.

14. The permanent magnet according to claim 12 wherein the direction of magnetization throughout each permanent magnet segment is the direction which, at the effective magnet center, provides the maximum contribution to the desired property optimizing the field.

15. The permanent magnet according to claim 12 wherein the size and position of the permanent magnet segments is selected so that the difference in the direction of magnetization direction between adjacent magnet segments is less than about 45°.

16. The permanent magnet according to claim 15 wherein the size and position of the permanent magnet segments is selected so that the difference in the direction of magnetization direction between adjacent magnet segments is less than about 30°.

17. The permanent magnet according to claim 10 wherein the magnetization direction throughout each permanent magnet segment is not constant.

* * * * *